United States Patent [19]

Peterson

[11] 4,334,074
[45] Jun. 8, 1982

[54] METHOD OF RECOVERING 3,6-DICHLOROPICOLINIC ACID FROM BASIC AQUEOUS SOLUTIONS OF SALTS THEREOF

[75] Inventor: Russell R. Peterson, Concord, Calif.

[73] Assignee: The Dow Chemical Company, Midland, Mich.

[21] Appl. No.: 230,783

[22] Filed: Feb. 2, 1981

[51] Int. Cl.$^3$ ........................................... C07D 213/55
[52] U.S. Cl. ................................. 546/327; 204/73 R; 204/98; 546/326
[58] Field of Search .............. 204/73 R; 546/315, 327

[56] References Cited

U.S. PATENT DOCUMENTS 3,317,549  5/1967  Johnston ............................. 546/315
4,087,431  5/1978  McGregor ........................... 546/327
4,217,185  8/1980  Kyriacou et al. ................... 204/292

Primary Examiner—Alan L. Rotman
Attorney, Agent, or Firm—R. R. Stringham

[57] ABSTRACT 3,6-Dichloropicolinic acid, a highly active plant growth regulator, is recovered from basic, aqueous solutions thereof by acidification with HCl in the presence of a flocculant, separating the precipitated 3,6-dichloroacid, extracting the unprecipitated acid from the mother liquor with a solvent and stripping the extracted acid from the solvent with another portion of the basic, aqueous feed solution.

11 Claims, 1 Drawing Figure

METHOD OF RECOVERING 3,6-DICHLOROPICOLINIC ACID FROM BASIC AQUEOUS SOLUTIONS OF SALTS THEREOF

BACKGROUND OF THE INVENTION 3,6-Dichloropicolinic acid, a highly active plant growth regulator, can be prepared by any of the methods disclosed in U.S. Pat. Nos. 3,317,549; 4,087,431 or 4,217,185. In the method of the U.S. Pat. No. 3,317,549 patent, the acid is obtained, as such, by hydrolysis of 3,6-dichloro-2-trichloromethyl pyridine with an aqueous solution of a mineral acid. In the methods of both of the other two patents, the 3,6-dichloropicolinic acid is obtained as a basic, aqueous solution of a salt—such as sodium 3,6-dichloropicolinate, for example—from which it is liberated ("sprung") as a solid, by acidification with a mineral acid.

The picolinate solution obtained in the method of the U.S. Pat. No. 4,087,431 patent is formed by refluxing 3,5,6-trichloro-4-hydrazino-picolinic acid with a solution of 2 to 3 molecular proportions of a base, such as sodium carbonate, in an aqueous medium, such as water or ethanol/water. The reaction mixture is cooled and acidified (any water-miscible solvents being removed). The resulting free 3,6-dichloropicolinic acid is recovered by filtration or is taken up in a water-immiscible solvent, such as dichloromethane, and then recovered by conventional procedures from the resulting solution. In commercial practice of the U.S. Pat. No. 4,087,431 process, organic solvents are not employed and about 80% of the picolinate formed is recovered as the free acid by heating the picolinate solution, acidifying it, cooling it slowly, filtering out the precipitated crystals and disposing of the filtrate (in an environmentally acceptable manner).

The picolinate obtained in the method of the U.S. Pat. No. 4,217,185 patent is formed by electrolytic reduction of tetrachloropicolinic acid in basic, aqueous solution, at an activated silver cathode. The free dichloro acid has been recovered in pilot plant operations, up to about 98% pure and in overall yields of up to 99% of theoretical, by extraction of the acidified picolinate solution with dichloromethane and evaporation of the extract. Such yields and purities are generally not economically reproducible on a commercial scale but at least give promise of bettering the results experienced in the commercial practice of the U.S. Pat. No. 4,087,431 process.

OBJECTS OF THE INVENTION

The primary object of the present invention is to provide a continuous process for recovering essentially all of the 3,6-dichloropicolinic acid present (in the form of an alkali metal salt) in basic, aqueous solutions thereof, such as, for example, those produced in the process of the U.S. Pat. No. 4,217,185 patent.

A further object is to provide such a process which can readily be adapted (at the expense of some decrease in product recovery) to upgrade impure 3,6-dichloropicolinate feeds thereto.

Another object is to provide a method of 3,6-dichloropicolinic acid recovery which can be carried out at ambient temperatures while also affording more rapid throughput rates than are attainable in the work-up procedures disclosed in the U.S. Pat. No. 4,087,431 and U.S. Pat. No. 4,217,185 patents.

An additional object is to make possible large-scale, economic recovery of the 3,6-dichloro acid from solutions thereof in basic, aqueous media.

Still other objects will be made apparent to those skilled in the art by the following specification and claims.

SUMMARY OF THE INVENTION

Figure 1:
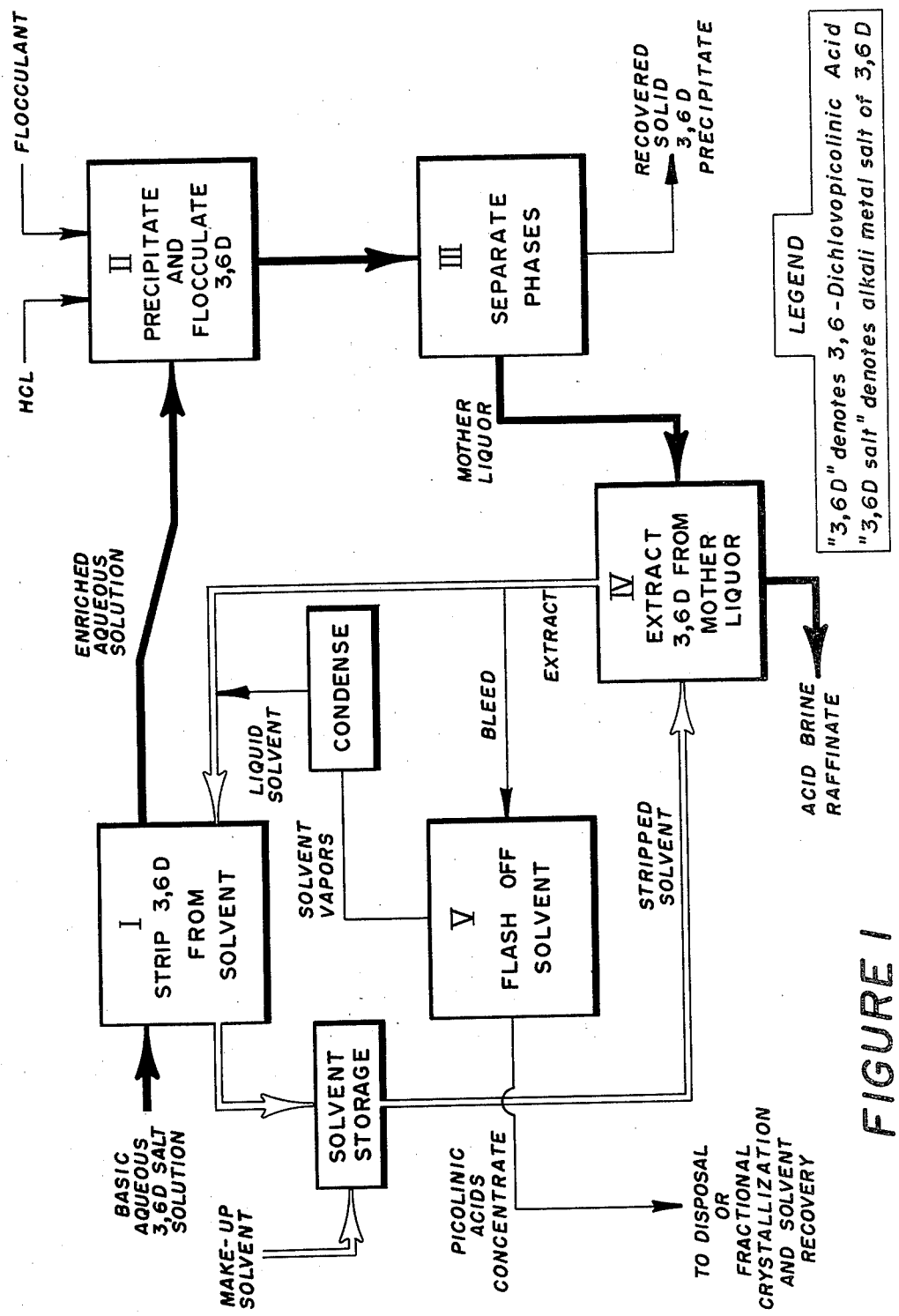
FIG. 1 is a block-type flow diagram for the recovery method of the present invention. The successive operations involved are denoted by the Roman numerals I–V employed in the following summary of the invention. Step V, as depicted, is specific to solvent removal from the bleed stream by flash distillation, but is intended to be representative of any suitable method of solvent separation.

It has now been discovered that the foregoing objects can be attained by:

I  contacting a basic aqueous 3,6-dichloropicolinate feed solution with a solution of free 3,6-dichloropicolinic acid in a water-immiscible solvent, thereby stripping the latter solution and enriching the former;

II  acidifying and adding a flocculant to the enriched picolinate solution, thereby precipitating most of the free acid, III  separating the precipitate, as a solid, from the aqueous mother liquor thereof, IV  extracting the dissolved free acid from the mother liquor with the stripped solvent, and treating more of the picolinate feed solution according to steps I–IV, employing the extract from step IV as the free acid solution in step I.

Optionally, in an additional step, V, the extract from step IV is treated to reduce its content of any co-extracted impurities, such as mono- or trichloropicolinic acids, for example, before it is recycled to step I.

The invention may be more specifically defined as: the method of recovering 3,6-dichloropicolinic acid from a basic, aqueous feed solution of an alkali metal salt thereof which comprises:

a. providing as said solution one containing the free hydroxide of said alkali metal, b. intimately contacting the aqueous solution with a solution of 3,6-dichloropicolinic acid in a water-immiscible solvent, thereby stripping the acid from said solvent and converting it to more of said salt, c. separating the thus-stripped solvent from the resulting mixture of the additional salt with said feed solution, d. adding to said mixture a flocculant and hydrochloric acid, the latter in an amount such as to reduce the pH of the mixture to a value of about 2 or less, thereby converting the alkali metal 3,6-dichloropicolinate present to the free acid and precipitating solid particles of free 3,6-dichloropicolinic acid, e. removing said particles from the resultant slurry, thereby producing an aqueous mother liquor having 3,6-dichloropicolinic acid dissolved therein, f. extracting the latter acid from said mother liquor by intimately contacting the liquor with said stripped solvent, then separating the resultant extract of 3,6-dichloropicolinic acid in said solvent, and g. employing the extract, as in the preceding step b, in treating more of said feed solution by said method.

DEFINITIONS

As used in the foregoing definition and elsewhere herein, the term "mixture" applies to picolinate solutions as such or as the liquid component of a slurry in which the solid component consists of undissolved picolinate particles.

By the term "aqueous solution" (of the alkali metal salt of 3,6-dichloropicolinic acid) is meant a solution comprising water and only such amounts of other liquids as do not detrimentally effect the operation of the process to an intolerable degree.

The term "water-immiscible solvent" is intended to denote a solvent which is not miscible with either the basic, picolinate feed solution or the acidified mother liquor of the precipitated free acid.

See also the discussion subsequently herein of Step IV.

DETAILED DESCRIPTION

Suitable Picolinate Feeds

The method of the invention may be practiced with any aqueous, alkali metal 3,6-dichloropicolinate feed solution which has a pH on the basic side and which does not include other substances in intolerable amounts. That is, the amounts of such other substances present in, or in admixture with, the picolinate solution are not such as to preclude essentially complete recovery of its picolinate content as 3,6-dichloropicolinic acid by the foregoing method. Neither are the amounts and kinds of those substances such as to result in impurity contents in the 3,6-dichloro acid which are so high as to render it unsuitable for its intended purpose.

Preferred such feeds are the basic, picolinate solutions formed in the 3,6-dichloropicolinate acid process disclosed in the foregoing U.S. Pat. No. 4,217,185 patent.

The 3,6-dichloropicolinate solution-producing step in the U.S. Pat. No. 4,087,431 process may be conveniently represented, for present purposes, as

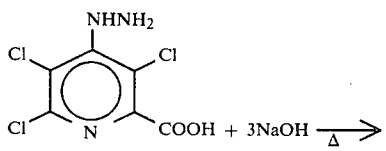

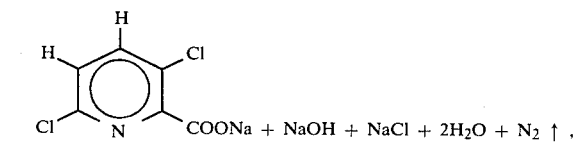

and the corresponding step in the U.S. Pat. No. 4,217,185 process similarly may be represented as

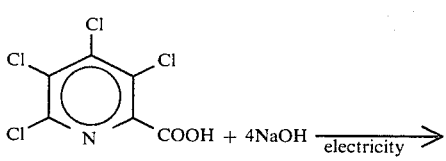

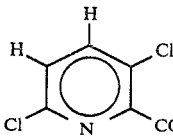
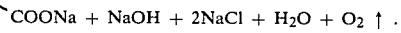

Both of the foregoing processes are carried out in aqueous media with excess base and produce basic, picolinate solutions containing alkali metal chlorides. The significant by-products in the two processes are different, however. Those formed in the process of the U.S. Pat. No. 4,087,431 patent account for a higher proportion of the starting material and generally include more hydrolysis products. In the U.S. Pat. No. 4,217,185 process, under- and over-reduction is more of a problem than hydrolysis, but a little 4-hydroxy-3,5,6-trichloropicolinic acid is formed (along with minor amounts of reduction by-products, i.e, the two isomeric trichloro- acids and/or at least one monochloroacid). In the total amounts (several percent or less) in which produced in the U.S. Pat. No. 4,217,185 process, the foregoing several impurities need not be removed for the ordinary herbicidal applications of 3,6D. However, a substantial reduction in impurities content can be effected by a variation in the method of the present invention.

The presence of the alkali metal chloride in the basic picolinate solution to be processed does not detrimentally effect stripping and is actually beneficial in reducing the amount of the free 3,6D which remains dissolved in the acidic mother liquor formed in the precipitation step.

Typical cell effluents from the U.S. Pat. No. 4,217,185 process contain about 7 wt. % 3,6 salt, about 2% NaOH, about 4% NaCl and up to about 1 percent of picolinate impurities.

Referring to FIG. 1, the method of recovering the 3,6D content from basic, aqueous 3,6D solutions will now be discussed.

Step I; Stripping Of Mother Liquor Extract

The aqueous picolinate feed solution has (or is adjusted to) a pH greater than 7 (preferably at least 9) and is intimately contacted with the 3,6D extract (from step IV) in a manner conventional for effecting interfacial reactions between solutes dissolved in two immiscible liquids. Contacting times and phase disengagement times of about 5 minutes each will generally be quite adequate.

Because the 3,6D (and any other picolinic acid) in the extract is entirely converted to the picolinate salt, which is not soluble to any appreciable extent in water-immiscible solvents, essentially complete stripping of the extract can be accomplished in one stage of contact. The minimum volume of feed solution required to strip a given volume of extract is that containing just sufficient of the free alkali metal hydroxide to salify the acids in the extract. However, more than this amount will be needed if said minimum volume of feed is not capable of dissolving all of the additional picolinate salt formed in the stripping step and it is desired that dissolution of the latter salt occur. (Since separation of the stripped extract from a solution is simpler than from a slurry, dissolution of the additional salt is considered preferable. That is, it is preferred that the mixture of the feed solution and the additional salt take the form of an enriched solution.)

It is contemplated that the present method will be carried out in a manner such as to produce wet cakes containing all of the picolinic acids present in basic, aqueous 3,6D solutions in which the weight ratio of mono- and/or trichloroacids to 3,6D is as high as about 1/20. However, the process can be adapted to more selectively recover 3,6D from feed solutions in which as much as about 10 wt. % of the picolinate species present are mono- and/or trichloropicolinates; this of course is at the expense of a reduced 3,6D recovery.

The alkali metal picolinate feed solution may be mixed with undissolved picolinate, i.e., may constitute the liquid component of a slurry. In general, though, it is considered highly preferable that all picolinate fed to the first step of the process be dissolved. It is particularly preferred that the picolinate solution be unsaturated, i.e., capable of dissolving the additional picolinate formed by salification of the free acids in the extract, during the stripping operation.

No substantial difficulties are anticipated for processing of feed solutions containing as much as 10 wt. % of the 3,6D alkali metal salt and up to 10 wt. % each of NaOH and NaCl.

Picolinate feed solutions in which alkali metal cations other than Na+ are present have not been subjected to the present process. Thus, although no reason is apparent why picolinate/hydroxide solutions in which the alkali metal cations are $K^{30}$, Rb+ or Cs+ should not be suitable, sodium picolinate/hydroxide solutions are preferred.

The stripping step ordinarily, and preferably, is carried out at ambient temperatures and atmospheric pressure. However, temperatures up to the boiling point of the solvent (or of the aqueous phase) at atmospheric or higher pressures may be employed. Similarly, lower temperatures, down to the point at which undesired salt precipitation, etc., occurs, may be employed.

Step II; Precipitation of Free 3,6D

Flocculant Requirements

In order to produce a readily separable precipitate at ambient temperatures, it is essential to introduce a flocculant (as well as the hydrochloric acid) to the enriched salt solution (or slurry); otherwise a thick, paste-like suspension results.

The flocculant and acid may be added in any manner or sequence which results in formation of 3,6D particles which can be readily separated from the mother liquor by decantation, filtration or centrifugation. Good results are obtained by adding the flocculant before the pH is lowered to the point (pH~2-3) at which precipitation starts; preferably, the pH is at least 7. Ordinarily, it is convenient to add the flocculant at pH's (about 9-10) typical of the cell effluents from the process of the U.S. Pat. No. 4,217,185 patent.

The preferred flocculant, an anionic flocculant—PURIFLOC A23, is marketed by The Dow Chemical Company and is a polyacrylamide having 20-25% of its pendant amide groups hydrolyzed to —COOH groups. However, any otherwise suitable coagulant which is not intolerably degraded by aqueous bases or acids may be employed as the flocculant. A variety of non-ionic, anionic and cationic flocculants are known. Anionic flocculants are considered best for the purposes of the present recovery method but no a priori reason for ruling out the use of non-ionic or cationic flocculants is apparent.

It is a simple matter, well within the skill of the art, to determine whether or not any candidate coagulant or flocculant will function in the manner of PURIFLOC A23. In each of several transparent beakers is placed equal portions of the basic, aqueous picolinate solution. The pH of each is adjusted, if necessary, to about 9 and the candidate material is added, in successively larger amounts (25, 50, 100 and 150 parts per million parts of solution, for example) to the different beakers. The pH of each solution is then lowered to about 1 by adding concentrated aqueous hydrochloric acid, with stirring. The resulting mixtures are allowed to stand. If the precipitated particles in a given mixture do not settle out in about 5 minutes or less, the amount of flocculant used in that test is considered inadequate. If the particles do settle out satisfactorily, decantation of the mother liquor is attempted. If this is not successful, filtration is attempted. If a satisfactory rate of filtration or a filter cake which can be handled readily is not obtained, separation by centrifugation is tried. Finally, if washing of the recovered 3,6D is contemplated, the solids separated by any of the foregoing techniques are washed (with cold 5% aq. HCl followed by ice water, for example) to determine whether peptization or other undesirable effects result.

The amount of flocculant required has been found to be dependent on the composition of the enriched feed solution entering the precipitation step (and may be expected to vary somewhat for different types of coagulants). The amount of PURIFLOC A23 required to attain essentially complete 3,6D settling in about 5 minutes (or less) increases from about 25 ppm to 100-150 ppm as the total content of mono- and/or trichloropicolinates in the enriched feed goes up from about 0.3 to about 1.5 wt. %. Impurity contents of greater than about 0.8% are not ordinarily encountered in cell effluents from the U.S. Pat. No. 4,217,185 process but steady state contents in the vicinity of 1.5 wt. % are reached, as a consequence of extract recycle, in the enriched effluents exiting Step I.

The mono- and trichloropicolinic acids are more soluble than 3,6D at the pH's typically established during the precipitation step. Thus, the impurities to 3,6D ratio in the mother liquor and in the solvent extract thereof tend, overall, to rise as the number of cycles increases. However, this in turn causes the relative content of impurities in the enriched picolinate solution to rise. Accordingly, the impurities to 3,6D ratio in the precipitate is the same, once a steady state condition has been established, as in the picolinate feed to the process. In other words, no purification is achieved if 100% of the 3,6D in the feed is recovered as product. This is of little concern for feeds of the type produced (as a cell effluent) by the method of the U.S. Pat. No. 4,217,185 patent because such feeds typically contain only a few percent or less of impurities. However, the steady state proportion of impurity acids in the picolinic acids component of the (acidified) enriched feed will be substantially higher (as much as about 16 wt. % monochloropicolinate, vs. about 4 wt. % in the picolinate component of the basic feed solution, for example) and a correspondingly greater amount (100-150 ppm, vs. 25 ppm or less, for example) of flocculant will be required than if the picolinic acids in the acidic mother liquor were not being recycled to the feed solution.

Operation of the present process in a manner which does achieve purification is discussed subsequently herein.

The flocculant may be added in any suitable manner but it is particularly convenient to add it as an aqueous mixture, such as, for example, a 0.25% solution of PURIFLOC A-23 in water. If the flocculant (coagulant) is stable as a solution or dispersion in the acid employed to effect precipitation, the flocculant and acid may be premixed and added as a single stream.

Acid Requirements

Substantial 3,6D precipitation does not occur unless the pH is dropped below a level of about 3, even when the content of alkali metal chloride in the acidified picolinate solution is as high as about 10 wt. %. The proportion of the 3,6D (and of the impurity acids) which remains dissolved in the mother liquor decreases as the pH is lowered but the additional amount of acid required to precipitate substantially more 3,6D than comes out of solution at a pH of about 1 is disproportionately large. (About 80% of the 3,6D precipitates at a pH of 1.)

Similarly, for reasons which will be apparent, it is highly advantageous to introduce the acid in a concentrated form. Ordinary, concentrated (38%) hydrochloric acid is eminently suitable, but the acid may be introduced as gaseous hydrogen chloride where desirable (as when the picolinate feed solution is unusually dilute, for example).

Although acids other than HCl could be considered for use in the present process, the introduction thereby of anions other than chloride to the system would appear to be undesirable. If the aqueous raffinate from Step IV is to be (neutralized and) utilized as a feed brine for electrolytic $NaOH/Cl_2$ production, the presence of more than incidental amounts of such other anions is ruled out.

Since operation of the precipitation step at ambient temperatures is a desideratum of the process, provision should be made for removing the heat liberated by the reaction between the acid and the alkali metal picolinate/hydroxide. If this is done by conventional heat exchange means, the requisite heat transfer will be more efficiently achieved if no solid phase is present. Thus, it is preferred, at least in the continuous mode of operation, to add the bulk of the acid in a first stage wherein the pH is not lowered far enough for precipitation to occur and heat exchange is readily accomplished. The partially acidified solution is then passed to the precipitation stage and the rest of the acid added. If desired, the effluent from the first stage may be pre-cooled far enough below ambient temperature so that the heat liberated in the second stage just suffices to restore the temperature of the mixture to ambient.

The acidification/precipitation ordinarily will be carried out in closed vessels at the autogenous pressure exerted by the mixture at the ambient temperature but may be carried out at higher pressures, or even at somewhat reduced pressures (if appropriate means for dealing with the evolved vapors are provided).

Sufficient residence time in the precipitation stage should be allowed for formation of well defined particles amenable to the contemplated method of phase separation. Good results have been experienced with residence times of about 0.5 hour and times of more than 1 hour do not appear to be necessary. Unless phase separation by decantation is contemplated, provision for particle settling need not be made. (However, production of 3,6D particles capable of rapid settling will generally be essential to either filtration or centrifugation.)

A sufficient degree of agitation to ensure rapid mixing of the acid and flocculant with the enriched picolinate solution (or slurry) can ordinarily be achieved without resort to intense stirring and may be attained by use of conventional means such as blades, circulating pumps, etc.

Step III; Phase Separation (etc.)

Any suitable method of phase separation may be employed but filtration is preferred as being rapid, relatively simple and readily adapted to truly continuous operation. If desirable, the mother liquor entrained in the recovered 3,6D (filter cake, for example) can be removed by conventional type washing procedures. The washed (or unwashed) product can readily be dried by ordinary methods. Neither washing or drying is necessary if the 3,6D is to be formulated as an aqueous solution (or dispersion) containing at least enough of a base (such as monoethanolamine, for example) to neutralize the hydrochloric acid in the entrained mother liquor.

Step IV; Extraction of 3,6D From The Mother Liquor

Suitable Solvents

The solvent presently preferred for the extraction is methylene chloride, which is stable, non-flammable and has physical properties particularly suitable for the purpose. However, any inert, liquid solvent for 3,6D which is water-immiscible (as defined earlier herein) and can readily be engaged with and disengaged from the aqueous picolinate and picolinic acid solutions may be employed for the extraction.

By an "inert" liquid is meant one which does not detrimentally react, with any of the materials it encounters in the process, to an intolerable extent.

By the term "solvent for 3,6D" is meant one which exhibits a sufficiently high 3,6D distribution ratio—vis a vis the acidic mother liquor—to be practical for commercial practice of the present invention.

Distribution Ratios; Solubilities

For example, when a pH 1 mother liquor, containing about 12 wt. % of NaCl and about 1 wt. % of 3,6D, is extracted with $CH_2Cl_2$, the distribution ratio (ratio of the equilibrium concentration of 3,6D in the organic phase to the concentration in the aqueous phase) is about 7.7 at 25° C. For an otherwise comparable mother liquor having an NaCl content of about 9 wt. %, the 3,6D distribution ratio is about 5.2 at 25° C.

Even at the latter ratio, the 3,6D content in the mother liquor can be reduced to about 50 ppm by (3 stage) extraction with about 2 volumes (total) of $CH_2Cl_2$ per volume of mother liquor.

The solubility of 3,6D in $CH_2Cl_2$, at 25° C., is about 4 grams per 100 grams of the solvent. That is, a 4% solution of 3,6D in $CH_2Cl_2$ is almost saturated. The aqueous, acidic (pH 1) mother liquor of course is saturated with 3,6D and typically will contain about 0.6 grams of 3,6D per 100 grams of the mother liquor, at 25° C.

The distribution ratios for the mono- and trichloropicolinic acids compare with the ratio for 3,6D about as follows, for $CH_2Cl_2$ extraction (at 25° C.) of mother liquors having NaCl content of from about 6 to 9%: 3,6D, about 5–6; mono-, about 3 and tri, about 44.

It will be recognized that it is not necessary for the 3,6D solvent to also be a solvent for the impurities present in the mother liquor. In fact, selective 3,6D extraction would be highly advantageous; the impurities could then be removed from the first raffinate by a second extraction operation with $CH_2Cl_2$ (the resulting second extract being stripped of solvent, rather than being recycled).

Effect of Mother Liquor Salinity

As indicated above, the 3,6D concentration in the extract is relatively higher when the dissolved alkali metal chloride content of the mother liquor is higher. Particular advantage can be taken of this "salting out" effect when the raffinate is to be utilized as a feed brine for an electrolytic $NaOH/Cl_2$ plant but is not saturated with NaCl. Some of the salt normally introduced directly to the latter plant is instead added to the picolinate stream, prior to or following Step I, thereby decreasing the solubility of 3,6D in the mother liquor. (It does not matter if the solubilities therein of the impurities is also decreased, unless upgrading of the product is contemplated.) Not only is the proportion of the 3,6D which precipitates increased, but extraction of the rest is facilitated and the volume of recycled extract is decreased.

Effect of Mother Liquor Temperature

It has been found that lower extraction temperatures result in higher distribution ratios.

For example, the distribution ratio for $CH_2Cl_2$ extraction of a pH 1 mother liquor (run 49, Table 1) containing about 12 wt. % NaCl is 5.18 at 35° C. but increases to 7.7 at 25° C. A desideratum of the present method is to avoid any need for refrigeration (which is expensive). However, full advantage should be taken of cool air or cool water availability, in order to carry out the extraction (and the precipitation, for that matter) at the lowest practical temperature.

Number of Extraction Stages

To minimize the volume of solvent and the contact time required for the extraction, multistage extraction is indicated. This can most conveniently be accomplished by use of three (or more) discrete mixer-settlers (in series) or a continuous extraction column equivalent to at least three theoretical stages.

Pressure Conditions

Although the extraction may be carried out at other than ambient pressures, no benefits of so doing are apparent and operation at normal atmospheric pressures is preferred.

Step V; Purification; Optional

The method of the present invention can be modified so that the impurity to 3,6D ratio is lower in the final product than in the picolinate feed to the process. In the ordinary practice of the invention, no advantage is realized from the difference in solubilities of the 3,6D and the impurities in the acidic brine component of the mother liquor. However, the latter difference can be utilized to effect purification by bleeding off a portion of the extract, flashing off most of the solvent from the bleed, and recombining the recovered solvent (plus makeup) with the rest of the extract (en route to Step I).

Although as much as 20% of the 3,6D in the acidified picolinate solution may not precipitate and is then transferred to the extract of the acidic mother liquor, only a fraction of the 3,6D going to the extract need be discarded (in the concentrate) in order to achieve a substantial reduction in the impurities content of the 3,6D product. That is, on repeated cycling, the ratio of impurities to 3,6D in the extract increases (until a steady state is achieved). Thus, if after a certain number of cycles (n, =5, for example) of batch operation, the next batch of extract is subjected to concentration and only the recovered solvent (plus makeup) forwarded to Step I, the 3,6D loss will be only about 20/n% but the relative decrease in the impurities content in the product will be substantially greater. Of course, to actually operate in this manner will have the result that a steady state will never be achieved and the product purity will go up and down. Ordinarily, it will be preferable to operate the process in a continuous mode and to bleed off a selected portion (say 1/5th, for example) of the extract for concentration, etc.

If desired, a substantial proportion of the 3,6D in the concentrate can be recovered by the following method, assuming the relative solubilities of 3,6D and the impurities in the extraction solvent used are about the same as when that solvent is $CH_2Cl_2$. The solvent content of the concentrate is established (by control of the solvent flash-off) at a level such that a monochloroacids-rich precipitate forms upon cooling the concentrate. The liquid phase is separated, concentrated further and cooled to produce a 3,6D-rich precipitate which is separated and redissolved in the recovered solvent to be combined with the main portion of the extract en route to Step I of the process. The trichloroacids-rich, final liquid is disposed of or, if the picolinate feed to Step I derives from the U.S. Pat. No. 4,217,185 process, further processed to recover the trichloroacids for recycle to the reduction, as by extraction with aqueous NaOH or by evporating off the solvent, for example.

The presence in the picolinate feed to Step I of typical amounts of hydrolysis products, such as the 3,5,6-trichloro-4-hydroxypicolinate, does not complicate 3,6D recovery in Steps II/III or from the concentrate produced in Step V; the hydroxy-acids are even more soluble in the acidified picolinate solution and less soluble in non-polar solvents than the other impurities.

It will be recognized that if at least a portion of the solvent in the bleed stream is to be recovered, it is desirable to employ a low boiling solvent, such as, for example, $-CH_2Cl_2$. However, any otherwise suitable solvent which can be flashed off at a temperature below the decomposition temperature of 3,6D may be used. Similarly, if recovery of 3,6D (and the trichloroacids) from the concentrate is contemplated, a solvent which has a low freezing point and in which the solubilities of the chloropicolinic acids decrease rapidly as the temperature is lowered is desirable, $CH_2Cl_2$ is particularly suitable in both of these respects.

Those knowledgeable in the art do not require additional details in order to carry out Step V or to further process the concentrate produced therein (for 3,6D and trichloroacids recovery) without resort to undue experimentation.

Identification of By-Products

As disclosed in the U.S. Pat. No. 4,217,185 patent, both of the isomeric trichloropicolinic acids are generally coproduced, in at least small amounts, with 3,6D.

The trichloroacids mixture consists predominantly (up to about 99 mole percent) of 3,5,6-trichlorochloropicolinic acid ("3,5,6-T"), which melts at 144° C. and can be separated from 3,4,6-T (melting at 128° C.) by known separatory techniques, such as preparative chromatography. Similarly, formation of three monochloropicolinic acid isomers, in about equal amount, is indicated by the available data (liquid/liquid chromatographic and mass spectrographic). These isomers have not have been unequivocally identified but are believed to be the 3-chloro (m.r. 127°-8° C.; 1-10% solubility in $H_2O$), 5-chloro-(m.r. 172°-3° C.; 10-25% solubility in $H_2O$) and 6-chloro-(m.r. 190°-190.5° C.; <1% solubility in $H_2O$) picolinic acids. 4-Hydroxy-3,5,6-trichloropicolinic acid melts at about 203° C. and is soluble in water to the extent of about 1-10%. (3,6D, recrystallized from benzene, has a melting range of 152°-3° C.)

The following examples are for purposes of illustration and are not to be construed as limiting the present invention in a manner inconsistent with the claims appended to these specifications.

EXAMPLES

Analytical Procedure

The procedure used to analyze all effluents of the type produced by the U.S. Pat. No. 4,217,185 process is as follows. The composition of the effluent is determined by gas phase chromatography (GPC). An aliquot of the effluent (usually an essentially homogeneous aqueous solution) is acidified to pH 1 and extracted three times with $CH_2Cl_2$. The combined extracts are dried over $Na_2SO_4$ and stripped in a rotary evaporator to a pot temperature of 45°-50° and the resulting solid (or semi-solid) residium dried in vacuo for 1 hour at 45° C., cooled and weighed. An approximately 0.1 gram sample is weighed out, combined with an equal weight of 1,2,3,4-tetrachlorobenzene (as an internal standard) and with 1 ml of BSA (N,O-bis(trimethylsilyl)acetamide). The resulting mixture heated in a REACTI-THERM reactor (Pierce Chemical Co.) for 10-15 minutes at 60° C., to convert the various picolinic acids to the corresponding trimethylsilyl esters. It is then injected in a GPC apparatus programmed for a preselected time/temperature profile-starting at 160° C. Detection is by means of thermal conductivity differences, the response factors for the several anticipated components of the sample having been predetermined with pure standard samples.

When the picolinic acid(s) have already been recovered, the steps in the foregoing procedure directed to that end are of course omitted.

All of the following experiments were carried out with one or more of the cell effluents (from the electrolytic preparation of 3,6D according to the U.S. Pat. No. 4,217,185 patent) listed in Table 1 below. Run 54 was deliberately terminated prematurely, so as to provide a higher than normal content of trichloroacids in the effluent. Run 55 was prolonged past "completion" to give an effluent with a higher than normal content of the monochloroacid(s). (A single such effluent of course will not have high contents of both under- and over-reduction products.)

Examples 1, 2 and 4 are of experiments which did not involve all of the steps specified in the definition of the present invention given earlier herein, and thus are not examples of "the invention" per se.

TABLE 1

| | Effluents From Electrolytic Reduction of Tetrachloropicolinic Acid | | | | | | | | | | | |
|---|---|---|---|---|---|---|---|---|---|---|---|---|
| | Wt. Percents in Effluent of: | | | | | | Percents[1] of Picolinates Which Are: | | | | | |
| | | | Na- Picolinates | | | | | | | | | |
| Run # | NaCl[4] | NaOH | Tet- | 4-OH | Tri- | Di- | Mono- | Tet- | 4-OH | Tri- | Di- | Mono- | Total |
| 47 | 1.78 | 2.2 | 0 | 0.15 | 0.07 | 3.18 | 0.02 | 0 | 4.4[2] | 2.0 | 93.1 | 0.5 | 3.42 |
| 49 | 3.98 | 5.9 | 0 | 0.07 | 0.11 | 6.79 | 0.23 | 0 | 0.9 | 1.59 | 94.33 | 3.18 | 7.20 |
| 54 | 3.32 | 0.9 | 0.14 | 0.06 | 0.57 | 5.50 | 0.16 | 2.2 | 1.0 | 8.80 | 85.50 | 2.50 | 6.43 |
| 55-B | 4.14 | 3.10 | 0 | 0 | 0 | 6.56 | 0.57 | 0 | 0 | 0 | 92.00 | 8.00 | 7.13 |
| 57 | 3.81 | 2.5 | 0 | 0.01 | 0.03 | 6.51 | 0.26 | 0 | 0.21 | 0.51 | 95.58 | 3.70 | 6.81 |

Explanation:
"Tet-" = Unconverted tetrachloropicolinic acid.
"4-OH" = 4-hydroxy-3,5,6-trichloropicolinic acid.
"Tri-" = Mixed trichloropicolinic acids.
"Di-" = 3,6-Dichloropicolinic acid.
"Mono" = Mixed monochloropicolinic acids.
NOTES:
[1] Normalized to total 100%.
[2] By difference, assuming 100% conversion of tet-acid.
[3] By difference, assuming incomplete tet-acid conversion.
[4] Calculated from stoichiometry of reactions by which the several picolinates are formed.

EXAMPLE 1

A. Effect of Effluent Composition on Flocculant Requirements in Steps II/III Measured volumes of a 0.25% aqueous solution of PURIFLOC A23 were added with stirring to 150 cc of the cell effluent in a 250 cc beaker. Concentrated hydrochloric acid was then added dropwise until the pH was lowered to 1.0. Stirring was stopped and the crystal characteristics of the precipitate observed. If the precipitate settled in less than five minutes, the crystals were rated as fast-settling. Otherwise they were rated as slow- or non-settling, as the case appeared to be. The results for the run 54, 55B and 57 effluents are given in Table 2 following. The flocculant concentrations given are parts by weight of solid PURIFLOC A23 per million parts of cell effluent.

TABLE 2
PURIFLOC Requirements For Rapid Settling

| Run # | % NaCl at pH 1 | Percent of Picolinates Which Is Mono- | Percent of Picolinates Which Is Tri- | PURIFLOC Concentration (ppm) 8.3 | 16.6 | 25 | 50 | 75 | 100 | 150 |
|---|---|---|---|---|---|---|---|---|---|---|
| 57 | 8.48 | 3.70 | 0.51 | non-settling | slow | fast | fast | fast | — | — |
| 54 | 6.24 | 2.50 | 8.80 | — | — | slow | slow | fast | fast | — |
| 55B | 9.54 | 8.00 | 0 | — | — | — | non-settling | — | slow | fast |

NOTES:
NaCl content includes that originally present in effluent and that formed by reactions of HCl with NaOH and Na-picolinate salts; calculated, assuming volume of 1000 grams effluent was 1 liter and HCl concentration is 0.1N at pH 1.

On the basis of other experience, the differences in NaCl content shown in the Table are not considered to have substantially contributed to the observed differences in flocculant requirements. Thus, it would appear that the flocculant concentration required for rapid settling is strongly influenced by the relative amounts of picolinates other than that of 3,6D present and is substantially more sensitive to the monochloropicolinate than to the other picolinates. (See also the last paragraph of Example 3, in this regard.)

B. Distribution of Major Picolinates Between Liquid and Solid Phases at pH 1

Each of the fast-settling mixtures from runs 54 and 55B was filtered on a Buchner funnel. The filtrands ("wet cakes") were oven-dried and analyzed as above-described.

The filtrates were each extracted with three 100 ml portions of $CH_2Cl_2$ and the combined extracts dried and stripped to yield residues which were analyzed in the same manner. The results are given in Table 3, below.

TABLE 3
Distribution Of Picolinic Acid Components Between Cake And Filtrate At 25° C.

| Run # | PURIFLOC Conc. (ppm) | % DOWCO 290 Distribution In Cake | % DOWCO 290 Distribution In Filtrate | % Mono Chloro Distribution In Cake | % Mono Chloro Distribution In Filtrate | % Tri Chloro Distribution In Cake | % Tri Chloro Distribution In Filtrate |
|---|---|---|---|---|---|---|---|
| 54 | 50 | 81.3 | 18.7 | — | — | 38.8 | 61.2 |
| 54 | 100 | 80.6 | 19.4 | — | — | 31.3 | 68.7 |
| 55B | 150 | 87.14 | 12.86 | 32.14 | 67.86 | — | — |

It is apparent that the proportion of the mono- and trichloroacid impurities remaining in solution (at a pH of 1) is considerably higher than the proportion of 3,6D.

EXAMPLE 2

Residence Time Required in Continuous, Stirred Crystallizer

A. A three-necked, round-bottomed flask was employed as a "crystallizer". The flask was tipped and positioned relative to a Buchner funnel to permit a continuous overflow from the lowermost neck into the funnel. The flask was charged to the overflow level with 90 ml of a slurry formed by acidification of a typical cell effluent (to which 75 ppm of PURIFLOC A23 had been added) to a pH of 1, with c. aq. HCl. Stirring (by means of a magnetic stirring bar) was commenced and dropwise addition (from separate dropping funnels mounted on the other two necks) of c. HCl and more of the flocculant-containing effluent was initiated. The rate of acid addition was such as to maintain the pH of the flask contents at a pH of 1 (as measured by a pH probe inserted through the overflow neck). The residence time in the flask was controlled by the rate of effluent addition and was reduced in steps (from a longer initial period) down to a period of one-half hour, without loss of ready filterability of the precipitate. Shorter residence times were not checked but are considered feasible.

It was found that it made no difference whether or not the pH of effluent feed (normally at least 13) was lowered to a pH of 10 (by acid addition) before being introduced to the crystallizer.

EXAMPLE 3

Simulated Continuous Operation, Including Recycle of Picolinic Acids Extracted From Acidic Mother Liquor of Recovered Solids To 150 cc of a cell effluent (Run 57) was added 50 ppm of PURIFLOC A23 (as a 0.25 wt. % aqueous solution) and enough c. aq. HCl to lower the pH to 1. The resulting precipitate was filtered out, washed with 20 cc of water and retained as (wet) cake #1. The combined filtrate (mother liquor) and wash was extracted in a separatory funnel with three 100 ml portions of $CH_2Cl_2$ and the raffinate retained as Brine #1. The combined extracts were stripped (of picolinic acids) by being shaken with another 150 ml of the effluent/flocculant solution. To the resulting, enriched picolinate feed solution was added 50 ppm of the flocculant and enough c. aq. HCl to lower the pH to 1, etc., the procedure being repeated until twelve wet cakes and brines had been produced. The amount of flocculant added to the enriched feed was adjusted as necessary to get a fast-settling precipitate in each cycle. The contents of 3,6D, mono- and trichloropicolinic acids were determined for each cake ($H_2O$ and NaCl-free basis) and for the solids obtained by evaporation of the final mother liquor extract. The results are given in Table 4.

TABLE 4
Simulated Continuous Operation Of Process (Steps I-IV)

| Cake # | Percent Mono- | Percent 3,6D | Percent Tri- | PPM PURIFLOC |
|---|---|---|---|---|
| 1 | 0.739 | 99.26 | — | 50 |
| 2 | 0.489 | 99.51 | — | 50 |
| 3 | 0.723 | 99.28 | — | 100 |
| 4 | 0.886 | 99.12 | — | 50 |

TABLE 4-continued

| Simulated Continuous Operation Of Process (Steps I-IV) | | | | |
|---|---|---|---|---|
| | Percent | | | PPM |
| Cake # | Mono- | 3,6D | Tri- | PURIFLOC |
| 5 | 4.180 | 95.83 | — | 50 |
| 6 | 0.747 | 99.25 | — | 75 |
| 7 | 1.130 | 98.86 | — | 75 |
| 8 | 3.410 | 96.59 | — | 75 |
| 9 | 0.957 | 99.05 | — | 75 |
| 10 | 2.159 | 97.84 | — | 100 |
| 11 | 0.480 | 99.52 | — | 100 |
| 12 | 1.163 | 98.84 | — | 100 |
| Solids From Extract Wt. 2.79 g. | 44.49 | 52.17 | 0.30 | — |

If the operation had been continued, the approximate amounts of the major picolinate salts formed (from the acids in the extract) in Step I would have been

| mono- | 0.4449 × 2.79 × 179.5/157.5 | = | 1.81 g. |
|---|---|---|---|
| 3,6D- | 0.5217 × 2.79 × 214/192 | = | 1.62 g. |
| tri- | 0.0030 × 2.79 × 248.5/226.5 | = | 0.01 g. |
| | | Total | 3.44 g. | and the amounts of these salts present in the effluent entering Step I would have been (refer to Table 1; 150 cc effluent assumed to weigh 150 g.) about

| mono- | 0.0026 × 150 | = | 0.390 g. |
|---|---|---|---|
| 3,6D- | 0.0651 × 150 | = | 9.765 g. |
| tri- | 0.0003 × 150 | = | 0.045 g. |
| | | Total | 10.200 g. | making the total amounts of these salts in the enriched effluent (152.79 grams) about

| mono- | 1.81 + 0.39 | = | 2.20 g. | (1.44% of effluent) |
|---|---|---|---|---|
| 3,6D | 1.62 + 9.77 | = | 11.39 g. | (7.45% of effluent) |
| tri- | 0.01 + 0.05 | = | 0.06 g. | (0.04% of effluent) |
| | | Total | 13.65 g. | |

Thus, the proportion of mono- in the picolinates component of the enriched feed entering Step II (in cycle 13) would have been about 2.20×100/13.65=16.12%, as compared to 0.39×100/10.20=3.82% in the picolinates component entering Step I (or entering Step II in the first "cycle").

Because it is evident from the data in Table 4 that a steady state was being approached at the end of the twelfth cycle, the proportion of monochloropicolinic acid(s) in the picolinates component of the feed entering Step II of the process would not be expected to go substantially higher.

In view of the data in Table 2, it is surprising that 100 ppm of the flocculant sufficed when the ratio of mono- to 3,6D during the precipitation was so high. It may be that the action of the flocculant is actually enhanced at such high levels of the monochloropicolinic acid(s).

EXAMPLE 4

Determination of Distribution Ratios

A weighed sample of effluent Run #55-B was acidified with c. aq. HCl to a pH of 1 and the resulting precipitate filtered out. The filtrate was weighed and extracted with a measured amount of $CH_2Cl_2$ in a separatory funnel at 25° C. The organic phase was separated, evaporated to dryness and the solid residue weighed and analyzed. Additional such extractions of the aqueous phase were carried out until essentially all of the picolinic acids had been extracted. The amounts of the acids in each phase were than calculated for each equilibration. A straight line, having a slope of 5.78, was obtained in plotting the equilibrium 3,6D concentrations in the two phases. When the experiment was repeated with effluent batch 54, a straight line was again obtained but with a somewhat lower slope (as would be expected from the difference in salinities of the two filtrates; see Table 2).

The respective distribution ratios (3.2 and 44.1) given earlier herein for the mono- and trichloropicolinic acids were determined from the analyses made on the extracted solids from Runs 55-B and 54, respectively.

What is claimed is:

1. The method of recovering 3,6-dichloropicolinic acid from a basic, aqueous feed solution of an alkali metal salt thereof which comprises:
   a. providing as said solution one containing the free hydroxide of said alkali metal,
   b. intimately contacting the aqueous solution with a solution of 3,6-dichloropicolinic acid in a water-immiscible solvent, thereby stripping the acid from said solvent and converting it to more of said salt,
   c. separating the thus-stripped solvent from the resulting mixture of the additional salt with said feed solution,
   d. adding to said mixture a flocculant and hydrochloric acid, the latter in an amount such as to reduce the pH of the mixture to a value of about 2 or less, thereby converting the alkali metal 3,6-dichloropicolinate present to the free acid and precipitating solid particles of free 3,6-dichloropicolinic acid,
   e. removing said particles from the resultant slurry, thereby producing an aqueous mother liquor having 3,6-dichloropicolinic acid dissolved therein,
   f. extracting the latter acid from said mother liquor by intimately contacting the liquor with said stripped solvent, then separating the resultant extract of 3,6-dichloropicolinic acid in said solvent, and
   g. employing the extract, as in the preceding step b, in treating more of said feed solution by said method.

2. The method of claim 1 in which said solvent is dichloromethane.

3. The method of claim 1 in which said alkali metal is sodium.

4. The method of claim 3 in which said flocculant is an anionic flocculant.

5. The method of claim 4 in which said flocculant is a partially hydrolyzed polyacrylamide.

6. The method of claim 5 in which said polyacrylamide is hydrolyzed to the extent of from about 20 to about 25 percent.

7. The method of claim 6 in which said solvent is dichloromethane.

8. The method of claim 7 in which the amount of hydrochloric acid added is such that the pH of said mother liquor is about 1.

9. The method of claim 8 in which said basic, aqueous feed solution is a cell effluent produced by electrolytic reduction of tetrachloropicolinic acid and also contains the sodium salt of a monochloropicolinic acid, the sodium salt of a trichloropicolinic acid or both.

10. The method of claim 9 in which sodium chloride is added to said feed solution, said mixture or to said mother liquor, thereby decreasing the solubility of 3,6-dichloropicolinic acid in the mother liquor.

11. The method of claim 9 including, as an additional step, diverting part of said extract as a bleed stream, removing dichloromethane therefrom to produce a picolinic acids concentrate and recombining the removed dichloromethane with the rest of said extract, thereby reducing the amount of the other said picolinic acids in said mixture, exiting step b, to a greater extent than the amount of 3,6-dichloropicolinic therein is reduced.

* * * * *

UNITED STATES PATENT AND TRADEMARK OFFICE
CERTIFICATE OF CORRECTION

PATENT NO. : 4,334,074
DATED : June 8, 1982
INVENTOR(S) : Russell R. Peterson

It is certified that error appears in the above—identified patent and that said Letters Patent is hereby corrected as shown below:

Column 3, line 38, delete "3,6-dichloropicolinate" and insert -- 3,6-dichloropicolinic --;

Column 4, line 33, delete "liquior" and insert -- liquor --;

Column 5, line 30, delete "$K^{30}$" and insert -- $K^+$ --;

Column 10, line 39, delete "evporating" and insert -- evaporating --;

Column 11, line 9, delete the last "have" in the line;

Column 16, line 7, delete "than" and insert -- then --.

Signed and Sealed this

Twelfth Day of October 1982

[SEAL]

Attest:

GERALD J. MOSSINGHOFF

Attesting Officer  Commissioner of Patents and Trademarks